United States Patent
Kurakata et al.

(10) Patent No.: US 6,569,877 B2
(45) Date of Patent: May 27, 2003

(54) THERAPEUTIC AND PROPHYLACTIC AGENTS FOR NEOPLASMS

(75) Inventors: Shinichi Kurakata, Tokyo (JP); Kosaku Fujiwara, Chofu (JP); Takashi Fujita, Kashiwa (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/053,136

(22) Filed: Jan. 18, 2002

(65) Prior Publication Data

US 2002/0137776 A1 Sep. 26, 2002

Related U.S. Application Data

(63) Continuation-in-part of application No. PCT/JP00/04858, filed on Jul. 19, 2000.

(30) Foreign Application Priority Data

Jul. 19, 1999 (JP) ............................................. 11-204476

(51) Int. Cl.[7] ..................... A61K 31/425; A61K 31/42; A61K 31/415
(52) U.S. Cl. ........................ 514/369; 514/376; 514/394
(58) Field of Search ................................. 514/369, 376, 514/394

(56) References Cited

U.S. PATENT DOCUMENTS

| 5,734,067 A | 3/1998 | Jinno et al. |
| 5,886,014 A | 3/1999 | Fujita et al. |
| 6,207,690 B1 * | 3/2001 | Urban et al. ................ 514/369 |
| 6,432,993 B1 * | 8/2002 | Fujita et al. ................ 514/369 |

FOREIGN PATENT DOCUMENTS

| EP | 1022272 A1 | 7/2000 |
| JP | 5-276895 | 10/1993 |
| JP | 8-259438 | 10/1996 |
| WO | WO 96/10021 | 4/1996 |
| WO | WO 99/30739 | 6/1999 |

* cited by examiner

*Primary Examiner*—Jerome D. Goldberg
(74) *Attorney, Agent, or Firm*—Frishauf, Holtz, Goodman & Chick, P.C.

(57) ABSTRACT

This invention relates to therapeutic and prophylactic agents for neoplasms which comprise a fused heterocyclic compound or a pharmaceutically acceptable salt thereof as an active ingredient; to the use of such a compound in the preparation of a medicament for the treatment and prevention of neoplasms; and to a method for treatment and prevention of neoplasms which comprises administering a pharmaceutically effective amount of such a compound to a warm-blooded animal (preferably a human).

42 Claims, No Drawings

THERAPEUTIC AND PROPHYLACTIC AGENTS FOR NEOPLASMS

This application is a continuation-in-part of International Application PCT/JP00/04858 filed Jul. 19, 2000 (not published in English) which is incorporated herein by this reference.

BACKGROUND OF THE INVENTION

This invention relates to therapeutic and prophylactic agents for neoplasms which comprise a fused heterocyclic compound or a pharmaceutically acceptable salt thereof as an active ingredient; to the use of such a compound in the preparation of a medicament for the treatment and prevention of neoplasms; and to a method for treatment and prevention of neoplasms which comprises administering a pharmaceutically effective amount of such a compound to a warm-blooded animal (preferably a human).

The term 'neoplasms' in this specification includes sarcoma, various cancers, and leukemia, which include fibrosarcoma, liposarcoma, osteosarcoma, angiosarcoma, cancers of the lung, the stomach, the large intestine, the breast, the prostate gland, the kidney, the liver, the pancreas, the esophagus, the tongue, the pharynx, the bladder and ovary, brain tumors, acute leukemia, chronic leukemia, and lymphoma.

The compounds which are useful for the present invention and general methods of preparing these compounds are described in Japanese Patent Application Publication Hei 9-295970, EP 0745600 and U.S. Pat. No. 5,886,014 (all incorporated by reference). However, these descriptions about these compounds do not disclose their suppressive effects against proliferation of cancer cells. Further, these compounds have been disclosed as therapeutic or prophylactic agents for diabetes mellitus or hyperlipidemia; thus, the prior art documents differ from the present invention.

Compounds having the benzimidazole ring group are disclosed in WO 99/18081. However, the fused hetero ring has phenoxy, phenylthio, pyridyloxy or pyridylthio groups as substituents. The present invention compounds do not have such substituents.

Numerous compounds are commercially available as chemotherapeutic agents for cancer. However, it has become clear that the efficacy of currently available chemotherapeutic agents against various cancers is sometimes insufficient, i.e., in some cases cancer cells have developed natural tolerance against the therapeutic agents. Further, some therapeutic or prophylactic agents exert side effects, or make cancer cells gain tolerance during clinical use. Therefore, clinical use of chemotherapeutic agents for cancers has been complicated. Under these circumstances, novel anticancer agents have always been desired in cancer chemotherapy.

The problem to be solved by the present invention is to provide novel anticancer agents to satisfy the desire described above.

The inventors have earnestly carried out research on the synthesis of fused heterocyclic compounds, pharmaceutically acceptable salts thereof, and their pharmacological activity in order to solve this problem. The inventors have found that some fused heterocyclic compounds exhibit excellent suppressive effects against proliferation of cancer cells and that they are excellent therapeutic and prophylactic agents for cancer.

BRIEF SUMMARY OF THE INVENTION

This invention comprises a therapeutic and prophylactic agent for neoplasms which comprises as active ingredient a fused heterocyclic compound of formula (I) or a pharmaceutically acceptable salt thereof:

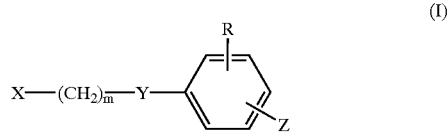

(I)

wherein
X is a benzimidazolyl group which is optionally substituted with 1 to 5 substituents selected from Group A;
Y is an oxygen or sulfur atom;
Z is a group selected from the following formulae:

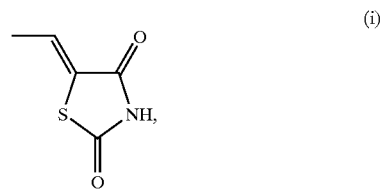

(i)

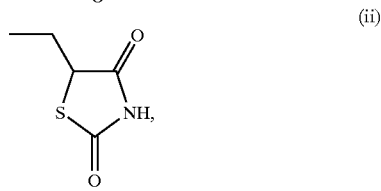

(ii)

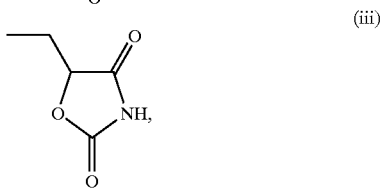

(iii)

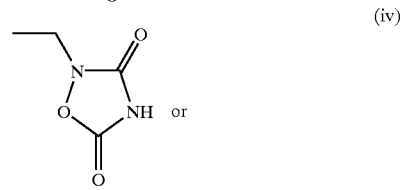

(iv)

or

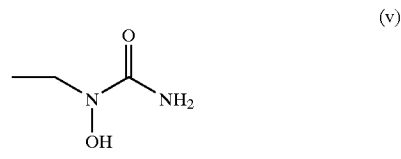

(v)

(hereinafter, these groups are referred to as i) 2,4-dioxothiazolidin-5-ylidenylmethyl, ii) 2,4-dioxothiazolidin-5-ylmethyl, iii) 2,4-dioxooxazolidin-5-ylmethyl, iv) 3,5-dioxooxadiazolidin-2-ylmethyl and v) N-hydroxyureidomethyl groups, respectively);

R is hydrogen, straight or branched chain $C_1$–$C_6$ alkyl, straight or branched chain $C_1$–$C_6$ alkoxy, halogen, hydroxyl, nitro, amino which is optionally substituted with one or more substituents selected from Group B and straight or branched chain $C_7$–$C_{11}$ aralkyl which is optionally substituted with one or more substituents selected from Group C;
m is an integer from 1 to 5 inclusive;

Group A comprises straight or branched chain $C_1$–$C_6$ alkyl, straight or branched chain $C_1$–$C_6$ alkoxy, straight or branched chain $C_7$–$C_{11}$ aralkyloxy, halogen, hydroxyl, straight or branched chain $C_1$–$C_{11}$ aliphatic acyloxy, straight or branched chain $C_1$–$C_6$ alkylthio, straight or branched chain $C_1$–$C_6$ halogenoalkyl, nitro, amino which is optionally substituted with one or more substituents selected from Group B, $C_6$–$C_{10}$ aryl which is optionally substituted with one or more substituents selected from Group C, and straight or branched chain $C_7$–$C_{11}$ aralkyl which is optionally substituted with one or more substituents selected from Group C;

Group B comprises straight or branched chain $C_1$–$C_6$ alkyl, straight or branched chain $C_7$–$C_{11}$ aralkyl, $C_6$–$C_{10}$ aryl, straight or branched chain $C_1$–$C_{11}$ aliphatic acyl, $C_8$–$C_{12}$ aromatic aliphatic acyl and $C_7$–$C_{11}$ aromatic acyl; and Group C comprises straight or branched chain $C_1$–$C_6$ alkyl, straight or branched chain $C_1$–$C_6$ alkoxy, halogen, hydroxyl, nitro, $C_6$–$C_{10}$ aryl, straight or branched chain $C_1$–$C_6$ halogenoalkyl, and amino which is optionally substituted with one or more substituents selected from Group B.

DETAILED DESCRIPTION OF THE INVENTION

Preferred compounds of formula (I) are:

(1) a fused heterocyclic compound or a pharmaceutically acceptable salt thereof wherein X is benzimidazolyl which is optionally substituted with 1 to 3 substituents selected from Group A;

(2) a fused heterocyclic compound or a pharmaceutically acceptable salt thereof wherein X is benzimidazolyl which is optionally substituted with two substituents selected from Group A;

(3) a fused heterocyclic compound or a pharmaceutically acceptable salt thereof wherein Y is an oxygen atom;

(4) a fused heterocyclic compound or a pharmaceutically acceptable salt thereof wherein Y is a sulfur atom;

(5) a fused heterocyclic compound or a pharmaceutically acceptable salt thereof wherein Z is 2,4-dioxothiazolidin-5-ylmethyl or 2,4-dioxooxazolidin-5-ylmethyl;

(6) a fused heterocyclic compound or a pharmaceutically acceptable salt thereof wherein Z is 2,4-dioxothiazolidin-5-ylmethyl;

(7) a fused heterocyclic compound or a pharmaceutically acceptable salt thereof wherein R is hydrogen, straight or branched chain $C_1$–$C_4$ alkyl, straight or branched chain $C_1C_4$ alkoxy, halogen, hydroxyl, nitro, amino, or straight or branched chain $C_7$–$C_{11}$ aralkyl;

(8) a fused heterocyclic compound or a pharmaceutically acceptable salt thereof wherein R is hydrogen;

(9) a fused heterocyclic compound or a pharmaceutically acceptable salt thereof wherein m is an integer from 1 to 3 inclusive;

(10) a fused heterocyclic compound or a pharmaceutically acceptable salt thereof wherein m is 1;

(11) a fused heterocyclic compound or a pharmaceutically acceptable salt thereof wherein Group A comprises straight or branched chain $C_1C_6$ alkyl, straight or branched chain $C_1C_6$ alkoxy, straight or branched chain $C_7$–$C_{11}$ aralkyloxy, halogen, hydroxyl, straight or branched chain $C_1$–$C_7$ aliphatic acyloxy, straight or branched chain $C_1C_6$ alkylthio and straight or branched chain $C_7$–$C_{11}$ aralkyl;

(12) a fused heterocyclic compound or a pharmaceutically acceptable salt thereof wherein Group A comprises straight or branched chain $C_1$–$C_4$ alkyl, straight or branched chain $C_1C_4$ alkoxy and straight or branched chain $C_7$–$C_{11}$ aralkyloxy;

(13) a fused heterocyclic compound or a pharmaceutically acceptable salt thereof wherein Group A comprises methyl, methoxy and benzyloxy;

(14) a fused heterocyclic compound or a pharmaceutically acceptable salt thereof wherein Group B comprises straight or branched chain $C_1C_4$ alkyl, straight or branched chain $C_7$–$C_{11}$ aralkyl and straight or branched chain $C_1$–$C_7$ aliphatic acyloxy; and

(15) a fused heterocyclic compound or a pharmaceutically acceptable salt thereof wherein Group C comprises straight or branched chain $C_1$–$C_4$ alkyl, straight or branched chain $C_1C_4$ alkoxy, halogen, hydroxyl, straight or branched chain $C_1$–$C_4$ halogenoalkyl and amino.

In addition, a preferred compound, which is included in the scope of compounds of formula (I), is a fused heterocyclic compound of formula (II) or a pharmaceutically acceptable salt thereof:

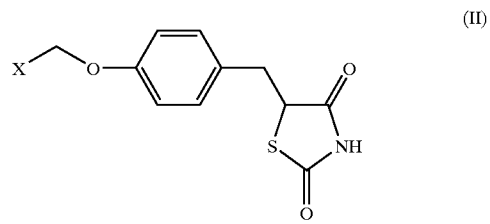

(II)

wherein X is benzimidazolyl which is optionally substituted with 1 to 5 substituents selected from Group A'; and Group A' comprises straight or branched chain $C_1$–$C_6$ alkyl, straight or branched chain $C_1$–$C_6$ alkoxy, straight or branched chain $C_7$–$C_{11}$ aralkyloxy, halogen, hydroxyl, straight or branched chain $C_1$–$C_7$ aliphatic acyloxy, straight or branched chain $C_1$–$C_6$ alkylthio and straight or branched chain $C_7$–$C_{11}$ aralkyl.

In the compound of formula (II), the number of substituents selected from Group A' is preferably from 1 to 3 and more preferably 2. In the compound of formula (II), the preferred Group A' is a group described in (12) or (13) above which is a preferred group of the substituent Group A.

Typical compounds of this invention are listed below in JP HEI-9-295970 and in U.S. Pat. No. 5,886,014 (especially Tables in columns 24–141). However, the scope of the invention is not restricted by these compounds.

5-[4-(1-methyl-1H-benzimidazol-2-ylmethoxy)benzyl]thiazolidine-2,4-dione;

5-[4-(6-methoxy-1-methyl-1H-benzimidazol-2-ylmethoxy)benzyl]thiazolidine-2,4-dione;

5-[4-(5-methoxy-1-methyl-1H-benzimidazol-2-ylmethoxy)benzyl]thiazolidine-2,4-dione;

5-[4-(1-benzyl-1-H-benzimidazol-5-ylmethoxy) benzyl]thiazolidine-2,4-dione;

5-[4-(5-hydroxy-1,4,6,7-tetramethyl-1H-benzimidazol-2-ylmethoxy)benzyl]thiazolidine-2,4-dione;

5-[4-(5-acetoxy-1,4,6,7-tetramethyl-1H-benzimidazol-2-ylmethoxy)benzyl]thiazolidine-2,4-dione;

5-[4-(6-benzyloxy-1-methyl-1H-benzimidazol-2-ylmethoxy)benzyl]thiazolidine-2,4-dione;

5-[4-(6-chloro-1-methyl-1H-benzimidazol-2-ylmethoxy)benzyl]thiazolidine-2,4-dione;

5-[4-(6-methylthio-1-methyl-1H-benzimidazol-2-ylmethoxy)benzyl]thiazolidine-2,4-dione; and pharmaceutically acceptable salts thereof.

A salt of the compound of formula (I) can be prepared by a conventional method. Examples of the salt include hydrohalogenic acid salts such as hydrofluoride, hydrochloride, hydrobromide and hydroiodide; inorganic acid salts such as nitrate, perchlorate, sulfate and phosphate; alkanesulfonic acid salts such as methanesulfonate, trifluromethanesulfonate and ethanesulfonate; arylsulfonic acid salts such as benzenesulfonate and p-toluenesulfonate; amino acid salts such as glutamate and aspartate; and carboxylic acid salts such as acetate, fumarate, tartrate, oxalate, maleate, malate, succinate, benzoate, mandelate, ascorbate, lactate, gluconate and citrate. Preferred salts are hydrohalogenic acid salts such as hydrofluoride, hydrochloride, hydrobromide and hydroiodide and a more preferred salt is hydrochloride.

In addition, when the compound of formula (I) has a phenolic hydroxyl group, a metal salt of the compound can be prepared by a conventional method. Examples of the salt include alkali metal salts such as lithium, sodium and potassium salts; alkaline earth metal salts such as calcium, barium and magnesium salts; and inorganic salts such as an aluminum salt.

The compounds of this invention can exist in various isomeric forms. For example, certain fused heterocyclic compounds of formula (I) have asymmetric carbon(s) on the thiazolidine or oxazolidine ring and also have asymmetric carbon(s) on the substituent(s) of said compound of formula (I). Such compounds can exist as optical isomers.

Certain fused heterocyclic compounds of formula (I) can exist as stereoisomers having (R) and (S) configuration(s) on each asymmetric carbon. The present invention encompasses each pure stereoisomer and a mixture of the isomers in any ratio. A pure stereoisomer of the fused heterocyclic compound of formula (I) can be synthesized from an optically active starting material or can be obtained from a mixture of synthesized fused heterocyclic compounds of formula (I) via a conventional optical resolution technique.

When certain fused heterocyclic compounds of formula (I) are allowed to stand in the air or recrystallized, such compounds absorb or adsorb water to form a hydrate. Such hydrates are encompassed in the scope of this invention.

In addition, certain fused heterocyclic compounds of formula (I) may absorb a solvent to form a solvate. Such solvates are also encompassed in the scope of this invention.

This invention encompasses a compound (prodrug) which converts into a fused heterocyclic compound of formula (I) or a pharmaceutically acceptable salt thereof in vivo. When the fused heterocyclic compound of formula (I) has a phenolic hydroxy group, a prodrug of the compound of formula (I) is a compound wherein the hydroxyl group is protected by a protecting group that can be cleaved by a biological process such as hydrolysis in vivo.

A protecting group that can be cleaved by a biological process such as hydrolysis in vivo is a group that is capable of being cleaved by a biological process to afford a compound having a free phenolic hydroxyl group or a salt thereof. Whether a compound of formula (I) has a protecting group that can be cleaved by a biological process can easily be determined. The hydroxy-protected compound of formula (I) under investigation is intravenously administered to a test animal such as a mouse or rat and the body fluids of the test animal are thereafter studied. If the parent compound of formula (I) having a free phenolic hydroxyl group or a salt thereof is detected in the body fluids of the test animal, the hydroxy-protected compound of formula (I) under investigation is judged to be a prodrug of the compound of formula (I).

Examples of such protecting groups include 1-(lower aliphatic acyloxy) lower alkyl groups such as formyloxymethyl, acetoxymethyl, propionyloxymethyl, butyryloxymethyl, pivaloyloxymethyl, 1-formyloxyethyl, 1-acetoxyethyl, 1-propionyloxyethyl, 1-butyryloxyethyl and 1-pivaloyloxyethyl; (lower alkoxycarbonyloxy)alkyl groups such as methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl and 1-(t-butoxycarbonyloxy)ethyl; and phthalidyl groups such as phthalidyl, dimethylphthalidyl and dimethoxyphthalidyl.

When the group Z in the compound of formula (I) is 2,4-dioxothiazolidin-5-ylmethyl, 2,4-dioxooxazolidin-5-ylmethyl, 2,4-dioxothiazolidin-5-ylidenylmethyl or 3,5-dioxooxadiazolidin-2-ylmethyl, these groups can exist in various tautomeric forms respectively. Examples of these tautomers are shown below.

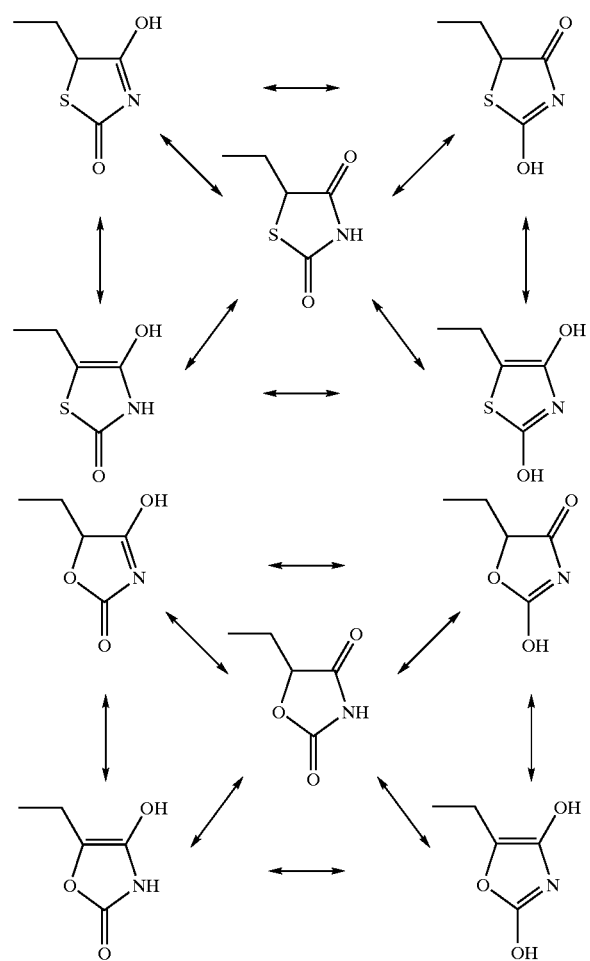

The compounds of formula (I) include each tautomer and a mixture of tautomers. Each tautomer and a mixture of tautomers are encompassed in the scope of this invention.

Dosage forms for the compounds of formula (I) include tablets, capsules, granules, powders or syrups for oral administration; and injections, suppositories and eyedrops for parenteral administration. These dosage forms can be prepared by a method known to those skilled in the art using additives such as excipients, lubricants, binders, disintegrants, stabilizers, corrigents and diluents. Examples of excipients include organic excipients, for example, sugar derivatives such as lactose, white soft sugar, glucose, mannitol and sorbitol; starch derivatives such as corn starch, potato starch, α-starch, dextrin and carboxymethylstarch;

cellulose derivatives such as crystalline cellulose, low-substituted hydroxypropylcellulose, hydroxypropylmethylcellulose, carboxymethylcellulose, calcium carboxymethylcellulose, internally cross-linked sodium carboxymethylcellulose; gum arabic; dextran; pullulan; inorganic excipients, for example, silicate derivatives such as light silicic anhydride, synthetic aluminum silicate and magnesium aluminate metasilicate; phosphates such as calcium phosphate; carbonates such as calcium carbonate; and sulfates such as calcium sulfate.

Examples of lubricants include stearic acid; metal stearates such as calcium stearate and magnesium stearate; talc; colloidal silica; waxes such as beeswax and spermaceti; boric acid; adipic acid; sulfates such as sodium sulfate; glycol; fumaric acid; sodium benzoate; DL-leucine, sodium salts of fatty acids; lauryl sulfates such as sodium lauryl sulfate and magnesium lauryl sulfate; silicic acid derivatives such as silicic acid anhydride and silicic acid hydrate; and the starch derivatives described above.

Examples of binders include polyvinylpyrrolidone, macrogol (trade mark) and the excipients described above.

Examples of disintegrants include the excipients described above and chemically modified starches and celluloses such as sodium croscarmellose, sodium carboxymethylstarch; and cross-linked polyvinylpyrrolidone.

Examples of stabilizers include paraoxybenzoates such as methylparaben and propylparaben; alcohols such as chlorobutanol, benzyl alcohol and phenethyl alcohol; benzalkonium chloride; phenol derivatives such as phenol and cresol; thimerosal; dehydroacetic acid; and sorbic acid.

Examples of corrigents include sweeteners, souring agents, and flavoring agents which are usually used.

The dose of the compound of formula (I) or pharmaceutically acceptable salt thereof will vary depending on a variety of factors such as the age, symptoms of the patient and the route of administration. A suitable dosage level for oral administration is from 0.01 mg (preferably 0.1 mg) per day as a lower limit to 2000 mg (preferably 500 mg, more preferably 100 mg) per day as an upper limit for a patient (warm-blooded animal, particularly a human) and the dosage is administered either as a single unit dosage or divided into several times throughout the day depending on the symptoms of the patient. A suitable dosage level for intravenous administration is from 0.001 mg (preferably 0.01 mg) per day as a lower limit to 500 mg (preferably 50 mg) per day as an upper limit for an adult (particularly an adult human), and the dosage is administered either as a single unit dosage or divided into several times throughout the day depending on the symptoms of the patient.

The following Examples, Reference Examples, Test Examples and Formulation Examples are intended to further illustrate the present invention and are not intended to limit the scope of this invention in any manner.

EXAMPLES

Example 1

5-[4-(6-Methoxy-1-methyl-1H-benzimidazol-2-ylmethoxy)benzyl]thiazolidine-2,4-dione hydrochloride A mixture of 5-[4-(6-methoxy-1-methyl-1H-benzimidazol-2-ylmethoxy)benzyl]thiazolidine-2,4-dione (10.6 g) and 4N hydrochloric acid in 1,4-dioxane (100 ml) was stirred at room temperature for 1 hour. The reaction mixture was concentrated, and to the residue was added ethyl acetate to form a precipitate. The precipitate was collected by filtration and washed with ethyl acetate to afford the title compound (11.0 g).

melting point: 275–277° C.

$^1$H NMR spectrum (DMSO-d$_6$, 400 MHz, δ ppm): 3.11 (1H, dd, J=14 Hz and 9 Hz), 3.34 (1H, dd, J=14 Hz and 4 Hz), 3.89 (3H, s), 3.98 (3H, s), 4.91 (1H, dd, J=9 Hz and 4 Hz), 5.64 (2H, s), 7.14 (2H, d, J=9 Hz), 7.15 (1H, d, J=9 Hz), 7.25 (2H, d, J=9 Hz), 7.50 (1H, s), 7.70 (1H, d, 9 Hz), 12.04 (1H, s, signal disappeared on addition of D$_2$O).

Example 2

5-[4-(6-Benzyloxy-1-methyl-1H-benzimidazol-2-ylmethoxy)benzyl]thiazolidine-2,4-dione hydrochloride 2-1

N-[2-[4-(2,4-dioxothiazolidin-5-ylmethyl) phenoxyacetylamino]-5-benzyloxyphenyl]-N-methylcarbamic acid t-butyl ester To a mixture of N-(2-amino-5-benzyloxyphenyl)-N-methylcarbamic acid t-butyl ester (2.29 g) (obtained in Reference Example 1), 4-(2,4-dioxothiazolidin-5-ylmethyl) phenoxyacetic acid (1.96 g) (obtained in Reference Example 6), triethylamine (0.97 ml) and anhydrous tetrahydrofuran (100 ml) was added diethyl cyanophosphonate (1.06 ml) and the resulting mixture was stirred at room temperature for 29 hours. The reaction mixture was concentrated and the residue partitioned between ethyl acetate and water. The ethyl acetate layer was dried over anhydrous sodium sulfate and evaporated in vacuo to give the crude desired product (4.27 g). 2—2

5-[4-(6-Benzyloxy-1-methyl-1H-benzimidazol-2-ylmethoxy)benzyl]thiazolidine-2,4-dione hydrochloride N-[2-[4-(2,4-Dioxothiazolidin-5-ylmethyl) phenoxyacetylamino]-5-benzyloxyphenyl]-N-methylcarbamic acid t-butyl ester (4.27 g) (obtained in Example 2-1) was dissolved in 4N hydrochloric acid in dioxane (30 ml) and the resulting mixture was allowed to stand at room temperature for 19 hours. The reaction mixture was concentrated and to the residue was added ethyl acetate to form crystals. The crystals were washed with ethyl acetate and dried in vacuo to afford the title compound (4.27 g).

melting point: 202–205° C.

Example 3

5-[4-(6-Chloro-1-methyl-1H-benzimidazol-2-ylmethoxy)benzyl]thiazolidine-2,4-dione hydrochloride 3-1

N-[2-[4-(2,4-Dioxothiazolidin-5-ylmethyl) phenoxyacetylamino]-5-chlorophenyl]-N-methylcarbamic acid t-butyl ester To a mixture of N-(2-amino-5-chlorophenyl)-N-methylcarbamic acid t-butyl ester (2.50 g) (obtained in Reference Example 2), 4-(2,4-dioxothiazolidin-5-ylmethyl) phenoxyacetic acid (3.01 g) (obtained in Reference Example 6), triethylamine (1.49 ml) and anhydrous tetrahydrofuran (50 ml) was added diethyl cyanophosphonate (1.75 g) and the resulting mixture was stirred at room temperature for 10 hours. The reaction mixture was concentrated and the residue partitioned between ethyl acetate and water. The ethyl acetate layer was washed with saturated aqueous sodium chloride solution, dried over anhydrous sodium sulfate and evaporated in vacuo. The resulting residue was chromatographed on a silica gel column using n-hexane/ethyl acetate (2/1) as the eluant to give the desired product (3.26 g). $R_f$=0.41 (thin-layer chromatography on a silica gel plate using n-hexane/ethyl acetate (2/3) as the eluant).

3-2

5-[4-(6-Chloro-1-methyl-1H-benzimidazol-2-ylmethoxy)benzyl]thiazolidine-2,4-dione hydrochloride N-[2-[4-(2,4-Dioxothiazolidin-5-ylmethyl)phenoxyacetylamino]-5-chlorophenyl]-N-methylcarbamic acid t-butyl ester (3.16 g) (obtained in Example 3-1) was dissolved in dioxane (30 ml). To the solution was added 4N hydrochloric acid in dioxane (30 ml) and the resulting mixture was stirred at room temperature for 3 hours and allowed to stand overnight. The reaction mixture was filtered and the crystals were washed with ethyl acetate and dried in vacuo to afford the title compound (2.44 g). softening point: 301–303° C.

Example 4

5-[4-(6-Methylthio-1-methyl-1H-benzimidazol-2-ylmethoxy)benzyl]thiazolidine-2,4-dione hydrochloride 4-1

N-[2-[4-(2,4-Dioxothiazolidin-5-ylmethyl)phenoxyacetylamino]-5-methylthiophenyl]-N-methylcarbamic acid t-butyl ester To a mixture of N-(2-amino-5-methylthiophenyl)-N-methylcarbamic acid t-butyl ester (2.0 g) (obtained in Reference Example 4), 4-(2,4-dioxothiazolidin-5-ylmethyl)phenoxyacetic acid (2.31 g) (obtained in Reference Example 6), triethylamine (1.14 ml) and anhydrous tetrahydrofuran (40 ml) was added diethyl cyanophosphonate (1.34 g) and the resulting mixture was stirred at room temperature for 4 hours and allowed to stand overnight. To the reaction mixture were further added 4-(2,4-dioxothiazolidin-5-ylmethyl)phenoxyacetic acid (0.84 g), triethylamine (0.3 g) and diethyl cyanophosphate (0.49 g) and the resulting solution was stirred at room temperature for 1.5 hours. At the end of this time the reaction mixture was concentrated and the residue was partitioned between ethyl acetate and water. The ethyl acetate layer was washed with saturated aqueous sodium chloride solution, dried over anhydrous sodium sulfate and evaporated in vacuo. The resulting residue was chromatographed on a silica gel column using n-hexane/ethyl acetate (2/1) as the eluant to give the desired product (3.54 g).

4-2

5-[4-(6-Methylthio-1-methyl-1H-benzimidazol-2-ylmethoxy)benzyl]thiazolidine-2,4-dione hydrochloride N-[2-[4-(2,4-Dioxothiazolidin-5-ylmethyl)phenoxyacetylamino]-5-methylthiophenyl]-N-methylcarbamic acid t-butyl ester (2.54 g) (obtained in Example 4-1) was dissolved in dioxane (25 ml). To the solution was added 4N hydrochloric acid in dioxane (25 ml) and the resulting mixture was stirred for 30 minutes at room temperature and allowed to stand for two nights. The reaction mixture was filtered and the crystals were washed with ethyl acetate and dried in vacuo to afford the title compound (2.98 g). softening point: 247–249° C.

Reference Example 1

N-(2-Amino-5-benzyloxyphenyl)-N-methylcarbamic acid t-butyl ester

To anhydrous DMF were added benzyl alcohol (2.48 ml) and 55% NaH (1.05 g) and then N-(2-nitro-5-chlorophenyl)-N-methylcarbamic acid t-butyl ester (5.73 g) was added in small portions. The resulting mixture was stirred at room temperature for 2 hours. The reaction mixture was concentrated and the residue partitioned between ethyl acetate and water. The extract was dried over anhydrous sodium sulfate and concentrated. The resulting residue was stirred in a mixture of dioxane (100 ml), water (10 ml), sodium hydrosulfite (20.9 g) and sodium hydrogencarbonate (21.0 g) at room temperature for 1 hour. The reaction mixture was partitioned between ethyl acetate and water and the extract was dried over anhydrous sodium sulfate and concentrated. The resulting residue was chromatographed on a silica gel column using ethyl acetate/n-hexane (1/2) as the eluant to afford the title compound (2.29 g). melting point: 86–89° C.

Reference Example 2

N-(2-Amino-5-chlorophenyl)-N-methylcarbamic acid t-butyl ester

A mixture of N-(2-nitro-5-chlorophenyl)-N-methylcarbamic acid t-butyl ester (6.0 g), dioxane (150 ml), water (30 ml), sodium hydrosulfite (14.6 g) and sodium hydrogencarbonate (17.6 g) was heated under reflux for 30 minutes. The reaction mixture was partitioned between ethyl acetate and water. The extract was washed with saturated aqueous sodium chloride solution, dried over anhydrous sodium sulfate and then concentrated. The residue was chromatographed on a silica gel column using ethyl acetate/n-hexane (1/3) as the eluant to afford the title compound (2.98 g). $R_f$=0.23 (thin-layer chromatography on a silica gel plate using ethyl acetate/n-hexane (1/3) as the eluant).

Reference Example 3

N-(2-Nitro-5-methylthiophenyl)-N-methylcarbamic acid t-butyl ester

To a suspension of sodium thiomethoxide (1.47 g) in anhydrous tetrahydrofuran (50 ml) was added dropwise a solution of N-(2-nitro-5-chlorophenyl)-N-methylcarbamic acid t-butyl ester (6.0 g) in anhydrous tetrahydrofuran (120 ml) while cooling at 0° C. The resulting mixture was stirred at 0° C. for 30 minutes and at room temperature for 1 hour. At the end of this time anhydrous DMF (30 ml) was added and the resulting mixture stirred at room temperature for 1 hour. DMF (20 ml) was added and then sodium thiomethoxide (0.73 g) and further DMF (50 ml) were added. The resulting mixture was stirred at room temperature for 7 hours. The reaction mixture was concentrated in vacuo and the residue was partitioned between ethyl acetate and aqueous sodium hydrogencarbonate solution. The extract was washed with saturated aqueous sodium chloride solution, dried over anhydrous sodium sulfate and concentrated to afford the desired compound (6.15 g).

Reference Example 4

N-(2-Amino-5-methylthiophenyl)-N-methylcarbamic acid t-butyl ester

To a solution of N-(2-nitro-5-methylthiophenyl)-N-methylcarbamic acid t-butyl ester (obtained in Reference Example 3) in anhydrous methanol (120 ml) and anhydrous tetrahydrofuran (30 ml) was added 10% palladium on carbon (3.0 g). The resulting mixture was vigorously stirred under a hydrogen atmosphere. Further 10% palladium on carbon (1.5 g) was added after 2.5 hours and 4.5 hours of the reaction respectively. The resulting mixture was stirred at room temperature for 1.5 hours and allowed to stand overnight. 10% palladium on carbon (0.7 g) was further added to the reaction mixture, which was then stirred under a hydrogen atmosphere for 1 hour. At the end of this time the 10% palladium on carbon was filtered off and the filtrate concentrated in vacuo. The residue was chromatographed on a silica gel column using ethyl acetate/n-hexane (⅓) as the eluant to afford the desired compound (3.61 g). $R_f$=0.24 (thin-layer chromatography on a silica gel plate using ethyl acetate/n-hexane (⅓) as the eluant).

Reference Example 5

4-(2,4-dioxo-3-tritylthiazolidin-5-ylmethyl) phenoxyacetic acid t-butyl ester To a solution of 5-(4-hydroxybenzyl)-3-tritylthiazolidine-2,4-dione (20.0 g) in acetonitrile (200 ml) was added cesium carbonate (21.0 g), followed by the addition of bromoacetic acid t-butyl ester (7.4 ml). The resulting mixture was stirred at 25° C. for 3 hours. To the reaction mixture was added water and the organic layer was separated and concentrated in vacuo. The residue was extracted with toluene and the extract was washed with diluted hydrochloric acid and water and concentrated in vacuo to afford the desired compound (24.9 g).

IR spectrum (KBr, vcm$^{-1}$): 1754, 1691, 1512, 1300, 1218, 1155, 740. $^1$H NMR spectrum (CDCl$_3$, 400 MHz, δ ppm): 1.48 (9H, s), 3.04 (1H, dd, J=14.2, 9.0 Hz), 3.43 (1H, dd, J=14.2, 3.9 Hz), 4.36 (1H, dd, J=9.0, 3.9 Hz), 6.83 (2H, d, J=8.5 Hz), 7.11 (2H, d, J=8.5 Hz), 7.15–7.35 (15H, m).

Reference Example 6

4-(2,4-dioxothiazolidin-5-ylmethyl)phenoxyacetic acid

To a solution of 4-(2,4-dioxo-3-tritylthiazolidin-5-ylmethyl)phenoxyacetic acid t-butyl ester (6.2 g) (obtained in Reference Example 5) in toluene (25 ml) was added p-toluenesulfonic acid monohydrate (204 mg). The resulting mixture was heated under reflux for 3 hours. Ethyl acetate (10 ml) was added while heating and then the mixture stirred at 25° C. for 1.5 hours. The resulting crystals were collected by filtration to afford the desired compound (2.5 g).

IR spectrum (KBr, vcm$^{-1}$): 3435, 3011, 1753, 1693, 1513, 1244, 1203. $^1$H NMR spectrum (DMSO-d$_6$, 400 MHz, δ ppm): 3.04 (1H, dd, J=14.2, 9.0 Hz), 3.30 (1H, dd, J=14.2, 4.3 Hz), 4.63 (2H, s), 4.86 (1H, dd, J=9.0, 4.3 Hz), 6.84 (2H, d, J=8.7 Hz), 7.15 (2H, d, J=8.7 Hz), 11.20 (1H, s), 12.94 (1H, br.s).

Test Example

Test Example 1

Antitumor Effects upon Human Large Intestine Cancer Cells COL-2-JCK.

Human cancer cells from the large intestine, COL-2-JCK (moderately differentiated adenocarcinoma), purchased from the Central Institute for Experimental Animals, were employed in the Test Example of the present invention as the solid tumor strain. The proliferated CLO-2-JCK cells were cultured and used for the experiments in our laboratory. In order to subculture the strain of the cancer cells and to test compounds in the experiments, the cancer cells were cultured with D-MEM/F-12 culture medium containing bovine fetal serum (manufactured by GIBCO Co.).

The test was carried out as follows: COL-2-JCK cells growed confluently on a petri dish for culture of cells (inner diameter 100 mm) were removed from the petri dish by using EDTA and 0.05% trypsin solution, and diluted to 100 cells/ml cell density with the culture medium. 3 ml of the diluted cell solution was then placed into each well of a 6-well plate (300 cells/well). At the same time, the test compound dissolved in DMSO solution was added so as to be 1, 10, 100 nM, 1 and 10 μM of the final concentrations to each well. The final concentration of the DMSO solution was adjusted to 0.1%. DMSO solution (0.1%) alone was placed in wells of the control group. After addition of the test compound, the cells were incubated in the presence of 5% CO$_2$ gas for 10 days at 37° C. After incubation was terminated, each well containing the cells was washed once with Dulbecco phosphate buffer saline (bivalent ion minus). Then 1 ml of 10% neutral formalin solution containing 0.02% crystal violet was added to the well and left for 5 minutes in order to stain the cells. After the dye was fixed, the cells were washed with water and air-dried. The total colony area (mm$^2$) of dye-fixed tumor cells was calculated by using an image analyzer of PCA-11 (manufactured by SystemSience Co.).

TABLE 1

| Test compound | Total colony area (mm$^2$) of tumor cells |  |  |  |  |  |
|---|---|---|---|---|---|---|
|  | final concentrations of the test compound |  |  |  |  |  |
| Example No. | 0 | 1 nM | 10 nM | 100 nM | 1 μM | 10 μM |
| 1 | 3311 | 2795 | 2018 | 1352 | 933 | 768 |

Test Example 2

Antitumor Effect on Human H69 Lung Cancer Cells.

A piece (5 mm×5 mm) of human lung affected by H69 strain of lung cancer was subcutaneously inoculated in a group of 10 BALB/c nude mice (female, 6 weeks old). The test compounds were suspended in 5% emulsified saline containing 2.5% dimethylacetamide. They were orally administered once a day for 24 times in total, i.e., from the first day after the inoculation to the 4th day, from the 7th to the 11th day, from the 14th to the 18th day and from the 21st to the 25th day and from the 28th to the 32nd day after inoculation.

The short diameter (mm) and the long diameter (mm) of the tumor were measured with an electronic digital caliper square on the 39th day after inoculation. The efficacy of the test compound was evaluated by calculation of the inhibitory growth rate of the tumor (GI %) according to the following equation:

$$GI(\%)=(1-A/B)\times 100$$

A: average tumor volume on the 39th day after inoculation in the group treated with the test compound (*)

B: an average tumor volume on the 39th day after inoculation in the non-treated group (*)

*: The tumor volume indicates ½×(long diameter of the tumor)×(short diameter of the tumor)².

The results are summarized in Table 2.

TABLE 2

| Test compound | dose (mg/kg) | GI (%) |
|---|---|---|
| Example 1 | 10 | 57 |

Test Example 3

Antitumor Effects on Human MKN-74 Stomach Cancer Cells.

A piece (5 mm×5 mm) of human stomach affected by MKN-74 strain of stomach cancer was subcutaneously inoculated in a group of 10 BALB/c nude mice (female, 6 weeks old). The test compounds were suspended in 5% emulsified saline containing 2.5% dimethylacetamide. They were orally administered once a day for 24 times in total, i.e., from the first day after inoculation to the 4th day, from the 7th to the 11th day, from the 14th to the $18^{th}$ day, from the 21st to the 25th day and from the 28th to the 32nd day after the inoculation.

The short diameter (mm) and the long diameter (mm) of the tumor were measured with an electronic digital caliper square on the 35th day after inoculation. The efficacy of the test compound was evaluated by calculation of the inhibitory growth rate of the tumor (GI %) in a similar to those described above in Test Example 2.

TABLE 3

| Test compound | dose (mg/kg) | GI (%) |
|---|---|---|
| example 1 | 10 | 76 |

Test Examples 1–3, show inhibitory activities against proliferation of the tumor cells. Therefore it is expected that compounds of the present invention will be potent prophylactic and therapeutic agents for cancers.

In particular, the compound of Example 1 of the present invention suppressed the proliferation of human stomach cancer cells to a remarkable extent, as shown by Test Example 3. This activity leads to the expectation of activity as a prophylactic and therapeutic agent for stomach cancer in warm blooded animals, especially in humans.

Formulation Examples

Formulations containing the compounds having general formula (I) or their salts as active ingredient can be prepared, for example, as follows:

Formulation Example 1

Powder

A powder can be made by pulverizing and mixing 4 g of 5-[4-(6-methoxy-1-methylbenzimidazol-2-ylmethoxy)benzyl]thiazolidine-2,4-dione hydrochloride (the compound of Example 1, hereinafter referred to as "compound A"), 10 g of polyvinylpyrrolidone, and 0.5 g of hydroxypropylmethylcellulose (trade mark: TC-5E; manufactured by Shin-etsu Chemical Industries Co.) by using an oscillatory mill for 30 min.

Formulation Example 2

Capsule

Twenty grams of compound A and 20 g of polyvinylpyrrolidone are dissolved in a mixture of 100 g of acetone and 100 g of ethanol. Granules can be obtained by aerification of the mixed solution with 200 g of sodium croscarmellose. 0.1 g of hydroxypropylmethylcellulose (Trade name: TC-5E, manufactured by Shin-etsu Chemical Industries Co.) and 1.9 g of lactose are mixed with 10 g of the granules. Filling a gelatin-made capsule with 0.24 g of the mixture affords a capsule. Each capsule contains 0.1 g of compound A.

Formulation Example 3

Tablet

One gram of the compound A and 1 g of polyvinylpyrrolidone are dissolved in mixture of 5 g of acetone and 5 g of ethanol. The organic solvent was then removed under reduced pressure by using a rotary evaporator. Fine granules are obtained by pulverization of the solid material obtained. One gram of the fine granules was mixed with 0.25 g of crystalline cellulose, 0.25 g of low substituted hydroxypropylcellulose, 0.05 g of hydroxypropylmethylcellulose (Trade name: TC-5E, manufactured by Shin-etsu Chemical Industries Co.), 0.18 g of lactose and 0.2 g of magnesium stearate. The tablets can be formed by use of a tabletting machine.

The fused heterocyclic compounds of formula (I) of this invention or pharmaceutically acceptable salts thereof exhibit excellent inhibitory activity against cancer-cell proliferation and are useful as agents for inhibiting cancer-cell proliferation in warm blooded animals, especially in humans.

Therefore, the fused heterocyclic compounds of formula (I) of this invention and pharmaceutically acceptable salts thereof are useful as therapeutic and prophylactic agents for cancers (especially, cancers of the large intestine, lung and stomach) in warm blooded animals, especially in humans.

What is claimed is:

1. A method for the treatment of cancer of the large intestine, lung or stomach in a warm-blooded animal, comprising administering to said warm-blooded animal in need of said treatment a pharmacologically effective amount of a fused heterocyclic compound of formula (I) or a pharmaceutically acceptable salt thereof:

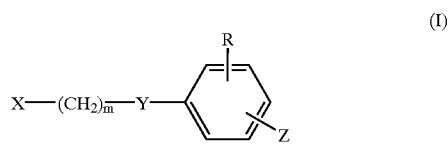

wherein

X is benzimidazolyl which is optionally substituted with 1 to 5 substituents selected from Group A;

Y is an oxygen or sulfur atom;

Z is a group selected from the following formulae:

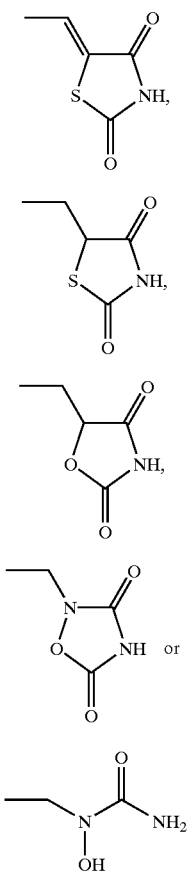

R is hydrogen, straight or branched chain $C_1$–$C_6$ alkyl, straight or branched chain $C_1$–$C_6$ alkoxy, halogen, hydroxyl, nitro, amino which is optionally substituted with one or more substituents selected from Group B, or straight or branched chain $C_7$–$C_{11}$ aralkyl which is optionally substituted with one or more substituents selected from Group C;

m is an integer from 1 to 5 inclusive;

Group A selected from the group consisting of straight or branched chain $C_1$–$C_6$ alkyl, straight or branched chain $C_1$–$C_6$ alkoxy, straight or branched chain $C_7$–$C_{11}$ aralkyloxy, halogen, hydroxyl, straight or branched chain $C_1$–$C_{11}$ aliphatic acyloxy, straight or branched chain $C_1$–$C_6$ alkylthio, straight or branched chain $C_1$–$C_6$ halogenoalkyl, nitro, amino which is optionally substituted with one or more substituents selected from Group B, $C_6$–$C_{10}$ aryl which is optionally substituted with one or more substituents selected from Group C and straight or branched chain $C_7$–$C_{11}$ aralkyl which is optionally substituted with one or more substituents selected from Group C;

Group B selected from the group consisting of straight or branched chain $C_1$–$C_6$ alkyl, straight or branched chain $C_7$–$C_{11}$ aralkyl, $C_6$–$C_{10}$ aryl, straight or branched chain $C_1$–$C_{11}$ aliphatic acyl, $C_8$–$C_{12}$ aromatic aliphatic acyl and $C_7$–$C_{11}$ aromatic acyl; and Group C selected from the group consisting of straight or branched chain $C_1$–$C_6$ alkyl, straight or branched chain $C_1$–$C_6$ alkoxy, halogen, hydroxyl, nitro, $C_6$–$C_{10}$ aryl, straight or branched chain $C_1$–$C_6$ halogenoalkyl and amino which is optionally substituted with one or more substituents selected from Group B.

2. The method of claim 1, wherein X is benzimidazolyl which is optionally substituted with two substituents selected from Group A.

3. The method of claim 1, wherein Y is an oxygen atom.

4. The method of claim 1, wherein Z is 2,4-dioxothiazolidin-5-ylmethyl.

5. The method of claim 1, wherein R is a hydrogen atom.

6. The method of claim 1, wherein m is 1.

7. The method of claim 1, wherein Group A comprises straight or branched chain $C_1$–$C_6$ alkyl, straight or branched chain $C_1$–$C_6$ alkoxy, straight or branched chain $C_7$–$C_{11}$ aralkyloxy, halogen, hydroxyl, straight or branched chain $C_1$–$C_7$ aliphatic acyloxy, straight or branched chain $C_1$–$C_6$ alkylthio and straight or branched chain $C_7$–$C_{11}$ aralkyl.

8. The method of claim 1, wherein Group A comprises straight or branched chain $C_1$–$C_4$ alkyl, straight or branched chain $C_1$–$C_4$ alkoxy and straight or branched chain $C_7$–$C_{11}$ aralkyloxy.

9. The method of claim 1, wherein Group B comprises straight or branched chain $C_1$–$C_4$ alkyl, straight or branched chain $C_7$–$C_{11}$ aralkyl and straight or branched chain $C_1$–$C_7$ aliphatic acyloxy.

10. The method of claim 1, wherein Group C comprises straight or branched chain $C_1$–$C_4$ alkyl, straight or branched chain $C_1$–$C_4$ alkoxy, halogen, hydroxyl, straight or branched chain $C_1$–$C_4$ halogenoalkyl and amino.

11. The method of claim 1, wherein:

X is benzimidazolyl which is optionally substituted with two substituents selected from Group A;

Y is an oxygen atom;

Z is 2,4-dioxothiazolidin-5-ylmethyl;

R is a hydrogen atom;

m is 1;

Group A comprises straight or branched chain $C_1$–$C_6$ alkyl, straight or branched chain $C_1$–$C_6$ alkoxy, straight or branched chain $C_7$–$C_{11}$ aralkyloxy, halogen, hydroxyl, straight or branched chain $C_1$–$C_7$ aliphatic acyloxy, straight or branched chain $C_1$–$C_6$ alkylthio and straight or branched chain $C_7$–$C_{11}$ aralkyl;

Group B comprises straight or branched chain $C_1$–$C_4$ alkyl, straight or branched chain $C_7$–$C_{11}$ aralkyl and straight or branched chain $C_1$–$C_7$ aliphatic acyloxy; and Group C comprises straight or branched chain $C_1$–$C_4$ alkyl, straight or branched chain $C_1$–$C_4$ alkoxy, halogen, hydroxyl, straight or branched chain $C_1$–$C_4$ halogenoalkyl and amino.

12. The method of claim 1, wherein:

X is benzimidazolyl which is optionally substituted with two substituents selected from Group A;

Y is an oxygen atom;

Z is 2,4-dioxothiazolidin-5-ylmethyl;

R is a hydrogen atom;

m is 1;

Group A comprises straight or branched chain $C_1$–$C_4$ alkyl, straight or branched chain $C_1$–$C_4$ alkoxy and straight or branched chain $C_7$–$C_{11}$ aralkyloxy;

Group B comprises straight or branched chain $C_1$–$C_4$ alkyl, straight or branched chain $C_7$–$C_{11}$ aralkyl and straight or branched chain $C_1$–$C_7$ aliphatic acyloxy; and Group C comprises straight or branched chain $C_1$–$C_4$ alkyl, straight or branched chain $C_1$–$C_4$ alkoxy, halogen, hydroxyl, straight or branched chain $C_1$–$C_4$ halogenoalkyl and amino.

13. The method of claim 1 for the treatment of cancer in a warm-blooded animal, comprising administering to said warm-blooded animal in need of said treatment a pharmacologically effective amount of a fused heterocyclic compound or a pharmaceutically acceptable salt thereof, wherein said fused heterocyclic compound is 5-[4-(1-methyl-1H-benzimidazol-2-ylmethoxy)benzyl]-thiazolidine-2,4-dione.

14. The method of claim 1 for the treatment of cancer of the large intestine, lung or stomach in a warm-blooded animal, comprising administering to said warm-blooded animal in need of said treatment a pharmacologically effective amount of a fused heterocyclic compound or a pharmaceutically acceptable salt thereof, wherein said fused heterocyclic compound is 5-[4-(6-methoxy-1-methyl-1H-benzimidazol-2-ylmethoxy)benzyl]-thiazolidine-2,4-dione.

15. The method of claim 1 for the treatment of cancer in a warm-blooded animal, comprising administering to said warm-blooded animal in need of said treatment a pharmacologically effective amount of a fused heterocyclic compound or a pharmaceutically acceptable salt thereof, wherein said fused heterocyclic compound is 5-[4-(5-methoxy-1-methyl-1H-benzimidazol-2-ylmethoxy)benzyl]-thiazolidine-2,4-dione.

16. The method of claim 1 for the treatment of cancer in a warm-blooded animal, comprising administering to said warm-blooded animal in need of said treatment a pharmacologically effective amount of a fused heterocyclic compound or a pharmaceutically acceptable salt thereof, wherein said fused heterocyclic compound is 5-[4-(1-benzyl-1H-benzimidazol-5-ylmethoxy)benzyl]thiazolidine-2,4-dione.

17. The method of claim 1 for the treatment of cancer of the large intestine, lung or stomach in a warm-blooded animal, comprising administering to said warm-blooded animal in need of said treatment a pharmacologically effective amount of a fused heterocyclic compound or a pharmaceutically acceptable salt thereof, wherein said fused heterocyclic compound is 5-[4-(5-hydroxy-1,4,6,7-tetramethyl-1H-benzimidazol-2-ylmethoxy)-benzyl]thiazolidine-2,4-dione.

18. The method of claim 1 for the treatment of cancer in a warm-blooded animal, comprising administering to said warm-blooded animal in need of said treatment a pharmacologically effective amount of a fused heterocyclic compound or a pharmaceutically acceptable salt thereof, wherein said fused heterocyclic compound is 5-[4-(5-acetoxy-1,4,6,7-tetramethyl-1H-benzimidazol-2-ylmethoxy)-benzyl]thiazolidine-2,4-dione.

19. The method of claim 1 for the treatment, of cancer in a warm-blooded animal, comprising administering to said warm-blooded animal in need of said treatment a pharmacologically effective amount of a fused heterocyclic compound or a pharmaceutically acceptable salt thereof, wherein said fused heterocyclic compound is 5-[4-(6-benzyloxy-1-methyl-1H-benzimidazol-2-ylmethoxy)benzyl]-thiazolidine-2,4-dione.

20. The method of claim 1 for the treatment of cancer in a warm-blooded animal, comprising administering to said warm-blooded animal in need of said treatment a pharmacologically effective amount of a fused heterocyclic compound or a pharmaceutically acceptable salt thereof, wherein said fused heterocyclic compound is 5-[4-(6-chloro-1-methyl-1H-benzimidazol-2-ylmethoxy)benzyl]-thiazolidine-2,4-dione.

21. The method of claim 1 for the treatment of cancer in a warm-blooded animal, comprising administering to said warm-blooded animal in need of said treatment a pharmacologically effective amount of a fused heterocyclic compound or a pharmaceutically acceptable salt thereof, wherein said fused heterocyclic compound is 5-[4-(6-methylthio-1-methyl-1H-benzimidazol-2-ylmethoxy) benzyl]-thiazolidine-2,4-dione.

22. A method for the treatment of cancer of the prostate in a warm-blooded animal, comprising administering to said warm-blooded animal in need of said treatment a pharmacologically effective amount of a fused heterocyclic compound of formula (I) or a pharmaceutically acceptable salt thereof:

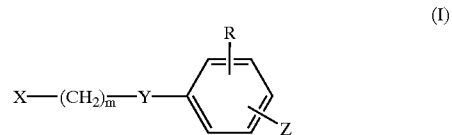

wherein
X is benzimidazolyl which is optionally substituted with 1 to 5 substituents selected from Group A;
Y is an oxygen or sulfur atom;
Z is a group selected from the following formulae:

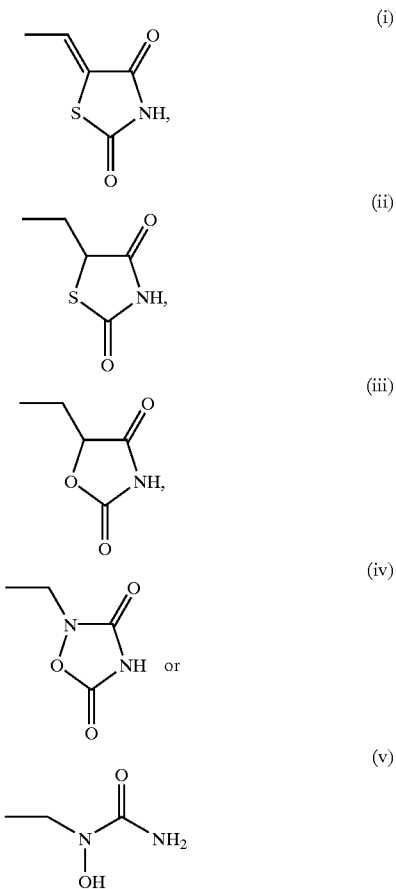

R is hydrogen, straight or branched chain $C_1$–$C_6$ alkyl, straight or branched chain $C_1$–$C_6$ alkoxy, halogen, hydroxyl, nitro, amino which is optionally substituted with one or more substituents selected from Group B, or straight or branched chain $C_7$–$C_{11}$ aralkyl which is optionally substituted with one or more substituents selected from Group C;

m is an integer from 1 to 5 inclusive;

Group A selected from the group consisting of straight or branched chain $C_1$–$C_6$ alkyl, straight or branched chain $C_1$–$C_6$ alkoxy, straight or branched chain $C_7$–$C_{11}$ aralkyloxy, halogen, hydroxyl, straight or branched chain $C_1$–$C_{11}$ aliphatic acyloxy, straight or branched chain $C_1$–$C_6$ alkylthio, straight or branched chain $C_1$–$C_6$ halogenoalkyl, nitro, amino which is optionally substituted with one or more substituents selected from Group B, $C_6$–$C_{10}$ aryl which is optionally substituted with one or more substituents selected from Group C and straight or branched chain $C_7$–$C_{11}$ aralkyl which is optionally substituted with one or more substituents selected from Group C;

Group B selected from the group consisting of straight or branched chain $C_1$–$C_6$ alkyl, straight or branched chain $C_7$–$C_{11}$ aralkyl, $C_6$–$C_{10}$ aryl, straight or branched chain $C_1$–$C_{11}$ aliphatic acyl, $C_8$–$C_{12}$ aromatic aliphatic acyl and $C_7$–$C_{11}$ aromatic acyl; and Group C selected from the group consisting of straight or branched chain $C_1$–$C_6$ alkyl, straight or branched chain $C_1$–$C_6$ alkoxy, halogen, hydroxyl, nitro, $C_6$–$C_{10}$ aryl, straight or branched chain $C_1$–$C_6$ halogenoalkyl and amino which is optionally substituted with one or more substituents selected from Group B.

23. The method of claim 22, wherein X is benzimidazolyl which is optionally substituted with two substituents selected from Group A.

24. The method of claim 22, wherein Y is an oxygen atom.

25. The method of claim 22, wherein Z is 2,4-dioxothiazolidin-5-ylmethyl.

26. The method of claim 23, wherein R is a hydrogen atom.

27. The method of claim 22, wherein m is 1.

28. The method of claim 22, wherein Group A comprises straight or branched chain $C_1$–$C_6$ alkyl, straight or branched chain $C_1$–$C_6$ alkoxy, straight or branched chain $C_7$–$C_{11}$ aralkyloxy, halogen, hydroxyl, straight or branched chain $C_1$–$C_7$ aliphatic acyloxy, straight or branched chain $C_1$–$C_6$ alkylthio and straight or branched chain $C_7$–$C_{11}$ aralkyl.

29. The method of claim 22, wherein Group A comprises straight or branched chain $C_1$–$C_4$ alkyl, straight or branched chain $C_1$–$C_4$ alkoxy and straight or branched chain $C_7$–$C_{11}$ aralkyloxy.

30. The method of claim 22, wherein Group B comprises straight or branched chain $C_1$–$C_4$ alkyl, straight or branched chain $C_7$–$C_{11}$ aralkyl and straight or branched chain $C_1$–$C_7$ aliphatic acyloxy.

31. The method of claim 22, wherein Group C comprises straight or branched chain $C_1$–$C_4$ alkyl, straight or branched chain $C_1$–$C_4$ alkoxy, halogen, hydroxyl, straight or branched chain $C_1$–$C_4$ halogenoalkyl and amino.

32. The method of claim 22, wherein:

X is benzimidazolyl which is optionally substituted with two substituents selected from Group A;

Y is an oxygen atom;

Z is 2, 4-dioxothiazolidin-5-ylmethyl;

R is a hydrogen atom;

m is 1;

Group A comprises straight or branched chain $C_1$–$C_6$ alkyl, straight or branched chain $C_1$–$C_6$ alkoxy, straight or branched chain $C_7$–$C_{11}$ aralkyloxy, halogen, hydroxyl, straight or branched chain $C_1$–$C_7$ aliphatic acyloxy, straight or branched chain $C_1$–$C_6$ alkylthio and straight or branched chain $C_7$–$C_{11}$ aralkyl;

Group B comprises straight or branched chain $C_1$–$C_4$ alkyl, straight or branched chain $C_7$–$C_{11}$ aralkyl and straight or branched chain $C_1$–$C_7$ aliphatic acyloxy; and Group C comprises straight or branched chain $C_1$–$C_4$ alkyl, straight or branched chain $C_1$–$C_4$ alkoxy, halogen, hydroxyl, straight or branched chain $C_1$–$C_4$ halogenoalkyl and amino.

33. The method of claim 23, wherein:

X is benzimidazolyl which is optionally substituted with two substituents selected from Group A;

Y is an oxygen atom;

Z is 2,4-dioxothiazolidin-5-ylmethyl;

R is a hydrogen atom;

m is 1;

Group A comprises straight or branched chain $C_1$–$C_4$ alkyl, straight or branched chain $C_1$–$C_4$ alkoxy and straight or branched chain $C_7$–$C_{11}$ aralkyloxy;

Group B comprises straight or branched chain $C_1$–$C_4$ alkyl, straight or branched chain $C_7$–$C_{11}$ aralkyl and straight or branched chain $C_1$–$C_7$ aliphatic acyloxy; and Group C comprises straight or branched chain $C_1$–$C_4$ alkyl, straight or branched chain $C_1$–$C_4$ alkoxy, halogen, hydroxyl, straight or branched chain $C_1$–$C_4$ halogenoalkyl and amino.

34. The method of claim 22, comprising administering to said warm-blooded animal in need of said treatment a pharmacologically effective amount of a fused heterocyclic compound or a pharmaceutically acceptable salt thereof, wherein said fused heterocyclic compound is 5-[4-(1-methyl-1H-benzimidazol-2-ylmethoxy)benzyl]-thiazolidine-2,4-dione.

35. The method of claim 22, comprising administering to said warm-blooded animal in need of said treatment a pharmacologically effective amount of a fused heterocyclic compound or a pharmaceutically acceptable salt thereof, wherein said fused heterocyclic compound is 5-[4-(6-methoxy-1-methyl-1H-benzimidazol-2-ylmethoxy)benzyl]-thiazolidine-2,4-dione.

36. The method of claim 22, comprising administering to said warm-blooded animal in need of said treatment a pharmacologically effective amount of a fused heterocyclic compound or a pharmaceutically acceptable salt thereof, wherein said fused heterocyclic compound is 5-[4-(5-methoxy-1-methyl-1H-benzimidazol-2-ylmethoxy)benzyl]-thiazolidine-2,4-dione.

37. The method of claim 22, comprising administering to said warm-blooded animal in need of said treatment a pharmacologically effective amount of a fused heterocyclic compound or a pharmaceutically acceptable salt thereof, wherein said fused heterocyclic compound is 5-[4-(1-benzyl-1H-benzimidazol-5-ylmethoxy)benzyl]thiazolidine-2,4-dione.

38. The method of claim 22, comprising administering to said warm-blooded animal in need of said treatment a pharmacologically effective amount of a fused heterocyclic compound or a pharmaceutically acceptable salt thereof, wherein said fused heterocyclic compound is 5-[4-(5-hydroxy-1,4,6,7-tetramethyl-1H-benzimidazol-2-ylmethoxy)-benzyl]thiazolidine-2,4-dione.

39. The method of claim 22 comprising administering to said warm-blooded animal in need of said treatment a pharmacologically effective amount of a fused heterocyclic compound or a pharmaceutically acceptable salt thereof, wherein said fused heterocyclic compound is 5-[4-(5-acetoxy-1,4,6,7-tetramethyl-1H-benzimidazol-2-ylmethoxy)-benzyl]thiazolidine-2,4-dione.

40. The method of claim 22 comprising administering to said warm-blooded animal in need of said treatment a pharmacologically effective amount of a fused heterocyclic compound or a pharmaceutically acceptable salt thereof, wherein said fused heterocyclic compound is 5-[4-(6-benzyloxy-1-methyl-1H-benzimidazol-2-ylmethoxy)benzyl]-thiazolidine-2,4-dione.

41. The method of claim 23 comprising administering to said warm-blooded animal in need of said treatment a pharmacologically effective amount of a fused heterocyclic compound or a pharmaceutically acceptable salt thereof, wherein said fused heterocyclic compound is 5-[4-(6-chloro-1-methyl-1H-benzimidazol-2-ylmethoxy)benzyl]-thiazolidine-2,4-dione.

42. The method of claim 22 comprising administering to said warm-blooded animal in need of said treatment a pharmacologically effective amount of a fused heterocyclic compound or a pharmaceutically acceptable salt thereof, wherein said fused heterocyclic compound is 5-[4-(6-methylthio-1-methyl-1H-benzimidazol-2-ylmethoxy)benzyl]-thiazolidine-2,4-dione.

* * * * *

UNITED STATES PATENT AND TRADEMARK OFFICE
CERTIFICATE OF CORRECTION

PATENT NO. : 6,569,877 B2
DATED : May 27, 2003
INVENTOR(S) : Kurakata et al.

It is certified that error appears in the above-identified patent and that said Letters Patent is hereby corrected as shown below:

Column 19,
Line 31, delete "23" and insert -- 22 --.

Column 20,
Line 5, delete "23" and insert -- 22 --.

Column 21,
Line 8, delete "23" and insert -- 22 --.

Signed and Sealed this

Twenty-second Day of February, 2005

JON W. DUDAS
*Director of the United States Patent and Trademark Office*